United States Patent [19]

Nakao et al.

[11] Patent Number: 5,360,789
[45] Date of Patent: Nov. 1, 1994

[54] THERAPEUTIC AGENT FOR SKIN OR CORNEAL DISEASE

[75] Inventors: Hiroshi Nakao; Takao Nagoya, both of Tuchiura; Yushi Saino, Tokyo, all of Japan

[73] Assignee: Kowa Co., Ltd., Nagoya, Japan

[21] Appl. No.: 50,330

[22] PCT Filed: Nov. 19, 1991

[86] PCT No.: PCT/JP91/01587
§ 371 Date: May 20, 1993
§ 102(e) Date: May 20, 1993

[87] PCT Pub. No.: WO92/08475
PCT Pub. Date: May 29, 1992

[30] Foreign Application Priority Data

Nov. 20, 1990 [JP] Japan ................... 2-314648

[51] Int. Cl.$^5$ ............................. A61K 37/02
[52] U.S. Cl. .................... 514/12; 530/350; 514/21
[58] Field of Search .............. 530/350; 514/12, 21

[56] References Cited

U.S. PATENT DOCUMENTS

| | | | |
|---|---|---|---|
| 4,873,222 | 10/1989 | Arai et al. | 514/21 |
| 4,937,324 | 6/1990 | Fujikawa et al. | 530/350 X |
| 5,116,942 | 5/1992 | Inoue et al. | 530/350 |
| 5,179,081 | 1/1993 | Iwasaki et al. | 514/12 |

FOREIGN PATENT DOCUMENTS 174023 7/1987 Japan.
020095 1/1989 Japan.

Primary Examiner—Michael G. Wityshyn
Assistant Examiner—C. Sayala
Attorney, Agent, or Firm—Oblon, Spivak, McClelland, Maier & Neustadt

[57] ABSTRACT

A therapeutic agent for skin or corneal diseases containing CPB-I (calphobindin-I) or recombinant CPB-I as the active ingredient. The CPB-I or recombinant CPB-I have excellent activities in promoting regeneration of granulation tissue, migration of corneal endothelial and epithelial cells, etc., and lowering PKC activity. Because the agent has an action mechanism different from that of the conventional agent, it can be used together with the conventional agent to enhance the therapeutic effect, thus being remarkably useful for treating all sorts of the skin and corneal diseases, in particular, wound and psoriasis.

13 Claims, 4 Drawing Sheets

THERAPEUTIC AGENT FOR SKIN OR CORNEAL DISEASE

TECHNICAL FIELD

The present invention relates to a therapeutic agent for skin or corneal diseases, and more specifically to a therapeutic agent for skin or corneal diseases, which contains CPB-I or recombinant CPB-I as an active ingredient and is useful for treating a skin or corneal disease such as a wound or psoriasis.

BACKGROUND ART

There have hitherto been provided a number of substances having a therapeutic effect on skin and corneal diseases, in particular, wounds. For example, growth factors (BIO/Technology, 135–140, 1985) such as an epidermal growth factor (EGF) (Exp. Cell Res., 164, 1–10, 1986), acid and basic fibroblast growth factors (acid and basic FGFs). (J. Surg. Res., 45, 145–153, 1988), transforming growth factors (TGF-α and TGF-β) (Japanese Patent Application Laid-Open No. 167231/1990; Science, 233, 532–534, 1986) and insulin-like growth factors (IGF-I and IGF-II), adhesion factors such as fibronectin, laminin and vitronectin (Ann. Rev. Biochem., 52, 961, 1983), and chemical substances such as retinoids and analogous compounds thereof (Am. J. Ophthalmol., 95, 353–358, 1983; Ann. Ophthal., 19, 175–180, 1987) have been known. The healing process of the skin wound is accompanied by granulation tissue formation, angiogenesis and re-epithelization. In these processes, fibroblasts, vascular endothelial cells and epidermal cells (keratinocytes) proliferate and migrate, respectively. The above-mentioned factors and other chemical substances have been known to be effective to the skin healing.

The healing process of the epithelia, parenchyma and endothelia of the cornea is accompanied by the migration and proliferation of epithelial cells, the phagocytosis of waste matter and the production of extracellular matrix by parenchymal cells, and the migration of endothelial cells, respectively.

In recent years, damages of endothelial cells have become recognized after cataract surgery, keratoplasty and wearing of contact lenses. Therefore, the importance of the endothelial cells has been pointed out. Human endothelial cells are said not to proliferate or to be hard to do. In their healing process, their migration and adhesion might be important. Up to the present, it has been reported that use of rabbit cultured endothelial cells which has proliferating ability revealed the fact that EGF and FGFs promote their proliferation. However, any effective remedy has not been yet reported. There is hence a demand for development of such an agent as promote the migration and adhesion of the endothelial cells.

On the other hand, as clinical pictures of skin diseases, in particular, psoriasis which is a chronic skin disease, there have been leukocyte infiltration (J. Invest. Dermatol., 68, 43–50, 1977), the hyperplasia of epidermis (J. Invest. Dermatol., 50, 254–258, 1968) and aberrant terminal differentiation (J. Invest. Dermatol., 70, 294–297, 1978), and as biochemical findings, there have been known, from the investigation on the mouse skins applied with a phorbol ester (TPA) which is a carcinogen, exhibiting psoriasis-like findings, the activation of protein kinase C (PKC) (J. Invest. Dermatol., 93, 379–386, 1989), increase in release of arachidonic acid and prostaglandin (Biochem. Biophys. Res. Commun., 92, 749–756, 1980), induction of ornithine dehydrogenase and transglutaminase activity (Cancer Res., 39, 4183–4188, 1979; Biochem. Biophys. Res. Commun., 97, 700–708, 1980) and increase in interleukin 1 (J. Invest. Dermatol., 88, 499A, 1987).

Steroid ointments and PUVA therapy have been used in local treatment for psoriasis, and dietetic therapy, vitamin $D_2$, vitamin $B_{12}$, etretinoids, etc. in general treatment. In recent years, TGF-β having an antiproliferative effect on keratinocytes (Japanese Patent Application Laid-Open No. 167231/1990) and cyclosporin A having an antiinflammatory effect (JAMA, 256, 3110–3116, 1986) have also been studied as therapeutic agents for psoriasis. However, action mechanisms thereof have not yet been clear.

Although the above-mentioned factors and chemical substances have been known as remedies for skin and corneal diseases such as wounds and psoriasis, their effects have been yet far from satisfactory.

It is considered to supplementarily use an agent having the different action mechanism in order to enhance the effect of the conventional agent, heal promptly and to cure completely in the therapy of a skin or corneal disease. However, any satisfactory agent has not been yet provided.

Therefore, it is an object of this invention to provide a therapeutic agent for skin or corneal diseases, which has an action mechanism different from that of the conventional agent and is excellent in therapeutic effect.

In view of the foregoing circumstances, the present inventors have carried out an extensive investigation. As a result, it has been found that CPB-I, (calphobindin-I) which is an anticoagulant, is excellent in therapeutic action on skin and corneal diseases, and its action mechanism is different from that of the conventional agent, leading to completion of the present invention.

DISCLOSURE OF THE INVENTION

The present invention is directed to a therapeutic agent for skin or corneal diseases containing CPB-I or recombinant CPB-I as the active ingredient.

BEST MODE FOR CARRYING OUT THE INVENTION

Figures 1A, 1B, 1C:
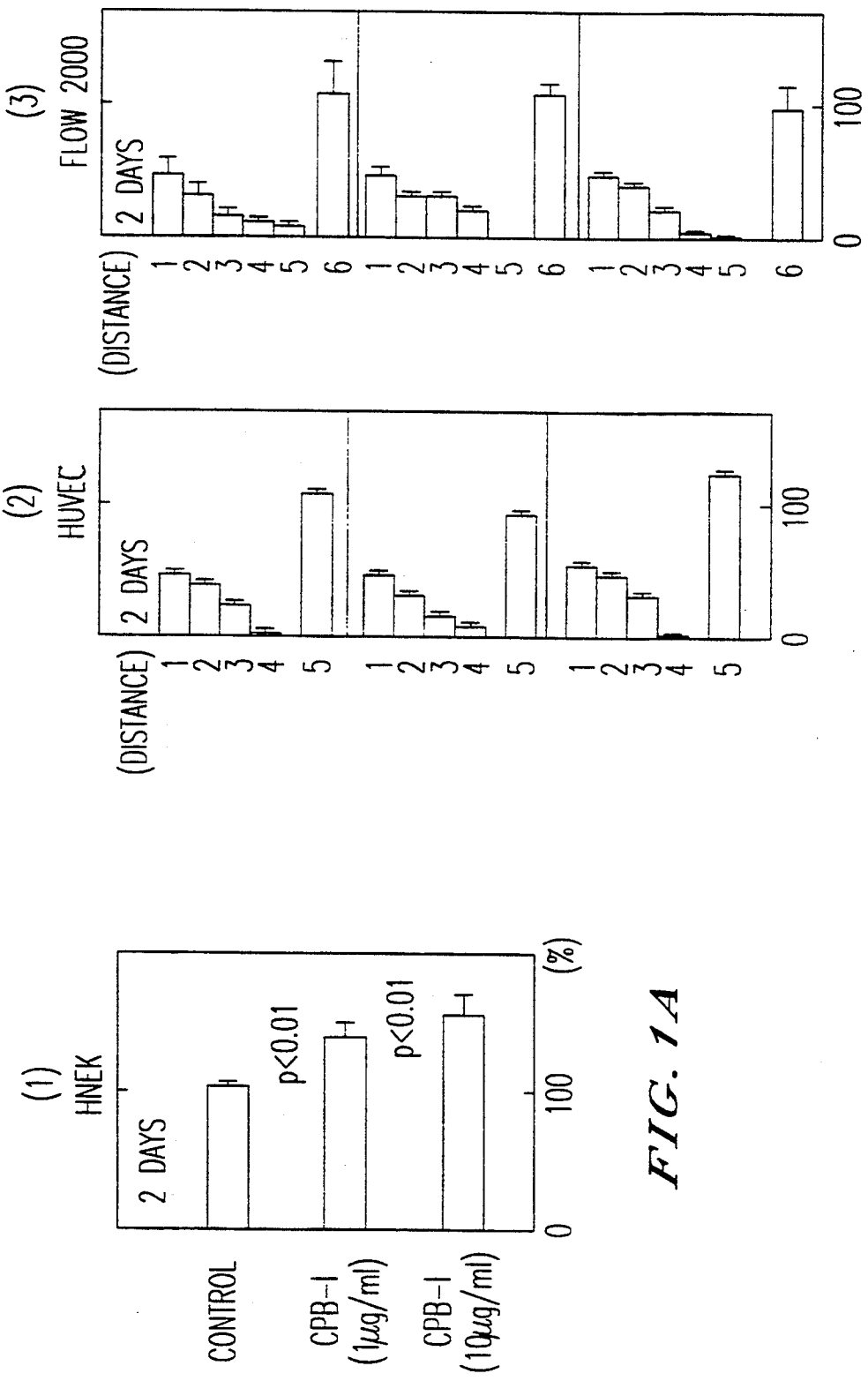
FIGS. 1A–1C are diagrams respectively illustrating the experimental results as to effect on the migration of HNEK, HUVEC and Flow 2000 in Experimental Example 1, respectively.

CPB-I which is an active ingredient in the therapeutic agent for skin or corneal diseases according to the present invention is an ubiquitous protein in the body, including the human placenta and secretary fluids (Chem. Pharma. Bull, 38, 1957–1960, 1990), exists in cytosol fraction in the cells and has physiological activities such as anticoagulant activity.

CPB-I can be extracted from human or animal organs (Japanese Patent Application Laid-Open No. 174023/1987). The thus obtained CPB-I has the following properties.

(1) Molecular weight (SDS-polyacrylamide gel electro-phoresis, in a reducing state):

34,000±2,000

(2) Isoelectric point (isoelectric column electrophoresis using an ampholite):

4.7±0.1

(3) Stability:
 (a) Deactivated by a heat treatment at 50° C. for 30 minutes
 (b) Stable at pH 4–10
 (c) Stable at 37° C. for 30 minutes in a plasma
(4) Action on blood coagulation system:
 (a) Extending recalcification coagulation time
 (b) Extending prothrombin time
 (c) Extending activated partial thromboplastin time
(5) Amino acid analysis:
By amino acid analysis, it is recognized that aspartic acid, threonine, serine, glutamic acid, proline, glycine, alanine, cystine, valine, methionine, isoleucine, leucine, tyrosine, phenylalanine, histidine, lysine and arginine exist.

CPB-I can be developed in *Escherichia coli* by a gene recombination technique making use of a gene fragment that codes for human or animal CPB-I (Japanese Patent Application Laid-Open No. 20095/1989). CPB-I is obtained by the gene recombination technique in the above-described manner (hereinafter referred to as "recombinant CPB-I") and its amino acid sequence is given in Japanese Patent Application Laid-open No. 20095/1989.

In addition to *Escherichia coli*, recombinant CPB-I can also be produced by using yeast (Japanese Patent Application Laid-Open No. 219875/1990).

The thus-obtained CPB-I and recombinant CPB-I have activity for healing the skin and corneal diseases.

For example, an investigation of the therapeutic action of CPB-I or recombinant CPB-I on a wound repair using cultured cells derived from human skin showed that it promotes the migration of keratinocytes, and has, as an adhesion factor, an activity comparable or equal to that of fibronectin on the keratinocytes and vascular endothelial cells. In the case that CPB-I or recombinant CPB-I is used for a wound in the rat skin, the regeneration of epidermis and granulation tissue is also promoted.

It is suggested from these results that CPB-I and recombinant CPB-I promote re-epithelization in wound repair, and in its turn facilitate angiogenesis and regeneration of granulation tissue, thereby exhibiting the overall promotion of healing. It is also considered that their action mechanisms are different from that of the conventional agent.

Since the conventional remedies are also used in the corneal wound in addition to the skin wounds, and the cornea is similar to the skin even in the kind of embryologically organized cells (epithelial, parenchymal and endothelial cells), CPB-I can be expected to act on the corneal wound.

Therefore, the effect of CPB-I on migration and adhesion was investigated using cultured endothelial cells of the rabbit cornea. In the migration, an effect comparable to those of EGF and fibronectin was recognized, and combination use with EGF enhanced the effect. It was hence suggested that its action mechanism is different from that of EGF. Although its effect on the adhesion is no match for that of fibronectin, it was recognized to have the activity of an adhesion factor. From these results, CPB-I can be expected to maintain the function of corneal endothelial cells by adding it to a preservative liquid for a cornea block of a donor upon keratoplasty, protect endothelial cells of the cornea or cure its wound by adding it to an intraocular irrigating solution or an infusion solution to an anterior chamber upon cataractous surgery, and in its turn promote the wound healing of the cornea.

In the meantime, the pathogenesis of psoriasis which is a chronic skin disease is not yet clear, so that there is no model animals therefor. It has however been known that the mouse skin applied TPA which is a carcinogen has psoriasis-like inflammation from the side view of biochemistry, activation of PKC, increase in release of arachidonic acid and prostaglandin, induction of ornithine dehydrogenase, transglutaminase activity and increase in interleukin 1. Although the keratinocytes are cultured in the presence of calcium in a low concentration (<0.15 mM), it is also known that the keratinocytes differentiate within several days if the concentration of calcium is increased to at least 1 mM (Cell, 19, 245–254, 1980). It is also known that at this time, the concentration of intracellular calcium increases (Carcinogenesis, 10, 777–780, 1989), and desmosomes then form in several hours (Cell, 19, 245–254, 1980). TPA is known to activate PKC (J. Invest. Dermatol., 92, 175–178, 1989), and to promote only a part of cultured keratinocytes to differentiate while promoting the residual cells to proliferate (Cancer Res., 42, 2344–2349, 1982). This action is consistent with that on the mouse skin.

Therefore, the therapeutic actions of CPB-I and recombinant CPB-I on psoriasis were investigated using cultured human keratinocytes from the side view of biology. More specifically, the actions of CPB-I or recombinant CPB-I on the intracellular PKC activity and PKC activation by TPA were investigated. As a result, it was found that these agents reduce the PKC activity in cytosol fraction and suppress PKC activation by TPA.

Cyclosporin A, a therapeutic agent for psoriasis, has no influence on the PKC activity (J. Invest. Dermatol., 93, 379–386, 1989), so that it is considered that the application of CPB-I or recombinant CPB-I singly or in combination with cyclosporin A be effective for psoriasis.

Therefore, it is expected that the treatment with CPB-I and recombinant CPB-I alone might be effective for a skin or corneal disease, and, furthermore, treatment combined with other therapeutic agents might be more effective.

CPB-I and recombinant CPB-I may preferably be contained in a proportion ranging from 0.01 to 100 mg, in particular, from 1 to 100 mg per 100 g of the therapeutic agent for skin or corneal diseases according to the present invention.

No particular limitation is imposed on the form of the therapeutic agent for skin and corneal diseases according to the present invention so long as it is in common use in pharmaceutical preparations. The agent may be in the form of a buffer solution, gel, cream, ointment, ophthalmic solution, ophthalmic ointment or the like.

CPB-I may be added to, for example, EP-II (product of Kaken Pharmaceutical Co., Ltd.) being in use at present as a preservative solution for a cornea block of a donor. In addition, CPB-I may be added to, for example, Opegard MA (product of Senju Seiyaku K.K.), BSS (product of Alcon Labs., Inc.), BSS Plus (product of Alcon Labs., Inc.) or an aqueous solution of hyaluronic acid, which are in use at present as an intraocular perfusion solution or a solution for infusing in an anterior chamber.

EXAMPLES

The present invention will hereinafter be described in more detail by the following experimental examples and examples.

Incidentally, in the experimental examples and examples, we have studied using CPB-I or recombinant CPB-I, obtained in accordance with Example 1 in Japanese Patent Application Laid-Open No. 174023/1987 or Example 4 in Japanese Patent Application Laid-Open No. 20095/1989, respectively.

Experimental Example 1 Action on Extension (1) Human normal epidermal keratinocytes (HNEK), (2) human normal umbilical vein endothelial cells (HUVEC), (3) fetal human lung-derived fibroblasts (Flow 2000) and (4) rabbit corneal endothelial cells [cultured from the cornea of New Zealand white rabbit in accordance with the method of Raymond G. M. et al. (Raymond G. M. et al., Invest. Ophthalmol. Vis. Sci., 27: 474–479 (1986))] were incubated to be confluent, respectively, in a keratinocyte cell growth medium (KGM) (product of Clonetics Company) containing a bovine pituitary extract (BPE), an endothelial cell growth medium (EGM) (product of Clonetics Company), an Eagle's minimum essential medium (E'MEM) containing 10% of fetal calf serum (FCS) and Medium 199 containing 10% of FCS and 10 ng/ml of mouse EGF. Cells on the opposite side from the center line were scraped out by a rubber policeman. After each well was washed with its corresponding medium, the medium was replaced by a medium containing CPB-I obtained in Referential Example 1. On that day and after two days, each well was recorded through a microscope. On the recorded image, distances migrated from wound edge in HNEK and the rabbit corneal endothelial cells, and cell numbers existing within certain distances from wound edge in HUVEC and Flow 2000 were measured or determined. The results as to the rabbit corneal endothelial cells and the results as to the other cells are shown in Table 1 and FIG. 1, respectively.

In each of FIGS. 1A–1C, the topmost bar graph represents the control group, the middle bar graph the group where the CPB-I concentration is 1 μg/ml, and the lowermost group where the CPB-I concentration is 10 μg/ml. In FIG. 1A, the horizontal axis represents the distance from the wound edge with the control being 100%. In FIG. 1A the horizontal axes represent the percentage of cells with the control being 100%. The numbers opposite bars within each group represent distance in μm as follows: 1: 0–333, 2: 334–666, 3: 667–1000, 4: 1001–1333, 5: 0–1333 (total). In FIG. 1C, the numbers along the horizontal and vertical axes have the same meaning as in FIG. 1B, except that the numerals 5 and 6 on the vertical axis represent distance in μm of 1334–1666 and 0–1666, respectively.

TABLE 1

| Effect on Migration of rabbit corneal endothelial cells | |
|---|---|
| | Distance from wound edge (μm) (mean ± S.E., n = 4) |
| Control | 69 ± 11 |
| EGF*[1] (5 ng/ml) | 170 ± 8 |
| EGF (50 ng/ml) | 218 ± 36 |
| EGF (500 ng/ml) | 229 ± 16 |
| CPB-I (10 μg/ml) | 138 ± 34 |
| CPB-I (50 μg/ml) | 183 ± 27 |
| CPB-I (100 μg/ml) | 201 ± 30 |
| FN*[2] (10 μg/ml) | 111 ± 38 |
| FN (50 μg/ml) | 142 ± 60 |
| FN (100 μg/ml) | 222 ± 25 |
| EGF (5 ng/ml) | 170 ± 8 |
| EGF + CPB-I (10 μg/ml) | 166 ± 14 |
| EGF + CPB-I (50 μg/ml) | 242 ± 30 |
| EGF + CPB-I (100 μg/ml) | 253 ± 16 |

*[1]Mouse EGF
*[2]Rabbit plasma fibronectin [prepared in accordance with Int. J. Cancer, 20, 1–5 (1977)]

From the above results, it was recognized that CPB-I promotes the migration of the corneal endothelial cells and, when used in combination with EGF, (PB-I further promotes the migration. It is also found from FIG. 1 that CPB-I promotes the migration of HNEK.

Experimental Example 2 Effect on Adhesion

HNEK, HUVEC, Flow 2000 and rabbit corneal endothelial cells, which were suspended in KGM, MCDB 151, E'MEM and Medium 199, respectively, were separately plated (1000 cells/well) on the well coated with CPB-I fibronectin or bovine serum albumin (BSA). Upon predetermined elapses of time, cells not adhering to each well were washed off with a Hanks' buffer solution, and the adherent cells were fixed with a 20% neutral buffered formalin fixative and then stained with hematoxylin and eosin (H.E.), thereby counting the number of adherent cells through a microscope. The results as to the rabbit corneal endothelial cells and the results as to the other cells are shown in Table 2 and FIG. 2, respectively.

TABLE 2

| | Effect on adhesion of rabbit corneal endothelial cells | | |
|---|---|---|---|
| Time (hr) | Number of Adherent Cells | | |
| | BSA*[3] | FN*[4] | CPB-I |
| 0.5 | 32 ± 5 | 261 ± 15 | 108 ± 8 |
| 1 | 47 ± 2 | 297 ± 10 | 109 ± 10 |
| 2 | 133 ± 8 | 312 ± 8 | 195 ± 13 |

*[3]Bovine serum albumin
*[4]Rabbit plasma fibronectin

Figure 2:
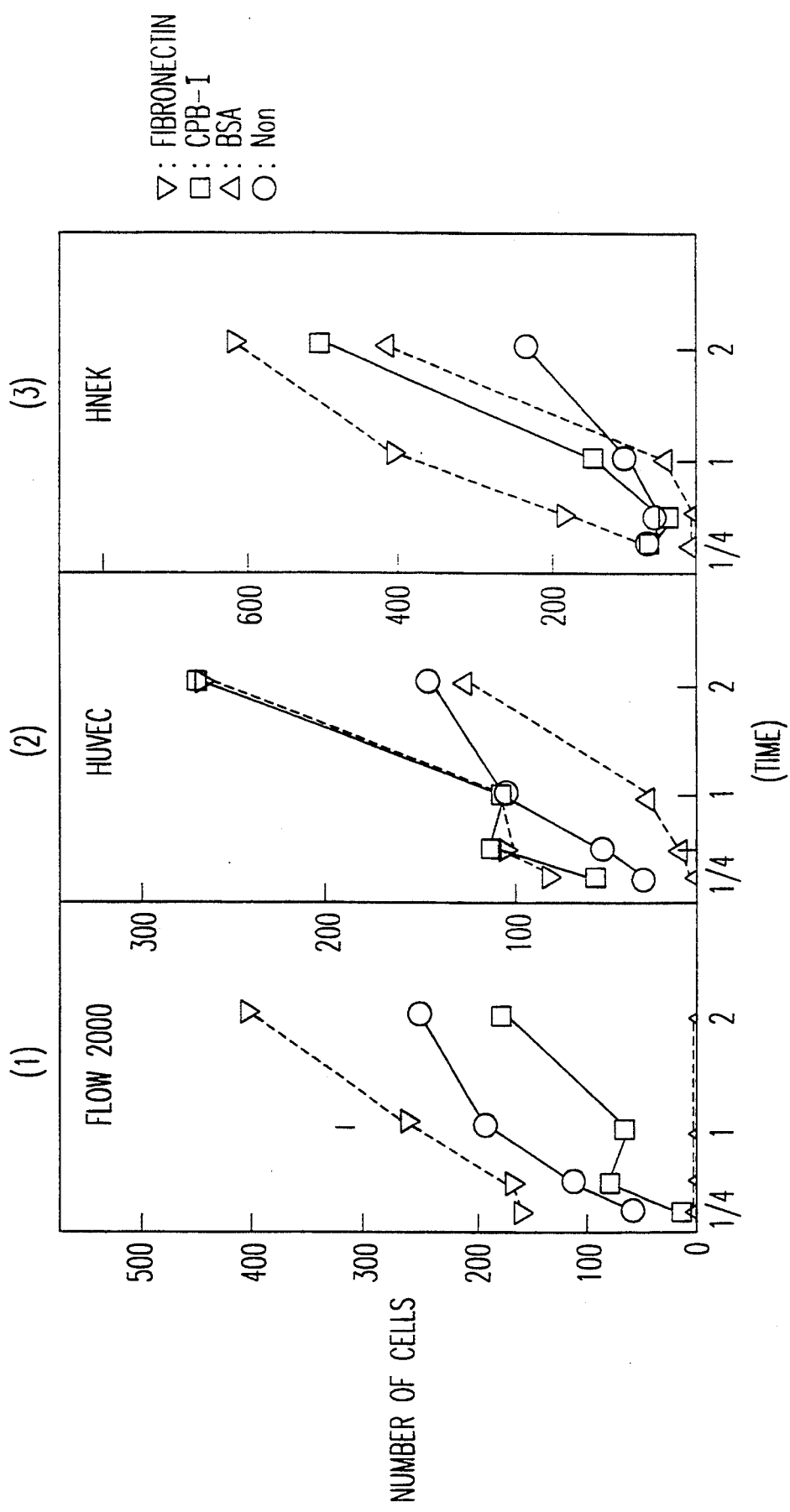
FIGS. 2(A)–(C) shows diagrams 1-3 respectively illustrating the experimental results as to effects on the adhesion of Flow 2000, HUVEC and HNEK in Experimental Example 2.

Table 2 and FIG. 2 indicate that CPB-1 certainly acts on cellular adhesion.

Experimental Example 3 Effect on Wound of Rat

Wister male rats aged 8 weeks were anesthesized with ether, and their dorsal hairs were shaved with an electric razor. Thereafter, a full-thickness round wound having a diameter of 9 mm was prepared using a trepane (Natsume Seisakusho). From the operation day, a phosphate buffer solution (PBS) containing CPB-I (PBS in a control group) was applied one time in the morning and one time in the evening each in an amount of 50 μl to the wounded site for 4 days. Upon the 4th day after wounding, the wounds were exercised and fixed in a 10% neutral buffered formalin. The tissue was embedded in paraffin, sectioned across the central part of the wound and stained with a hematoxylin and eosin (H.E.). The section was photographed through a microscope and the length of epidermal regeneration was measured, magnifying at $\times 23$. Area of a granulation tissue was estimated copying the photograph enlarged 23 times, cutting off a site of granulation tissue and then weighing it. The number of capillary in the granulation tissue was counted through the microscope. The results are shown in Table 3.

TABLE 3

| Treatment | Number of Specimens (n) | Epidermal regeneration (mm) | Granulation Tissue Area (mm$^2$) | Number of Capillary vessls (n/mm$^2$) |
| --- | --- | --- | --- | --- |
| Control group | 10 | 1.660 ± 0.114 | 4.36 ± 0.52 | 110.3 ± 9.0 |
| CPB-I (10 μg/rat) | 10 | 1.747 ± 0.140 | 5.18 ± 0.37 | 97.3 ± 7.9 |
| CPB-I (100 μg/rat) | 9 | 2.198 ± 0.160 (p < 0.01) | 5.26 ± 0.31 | 103.1 ± 12.3 |

Table 3 indicates that CPB-I promotes the regeneration of epidermis, granulation and angiogenesis.

Figure 3:
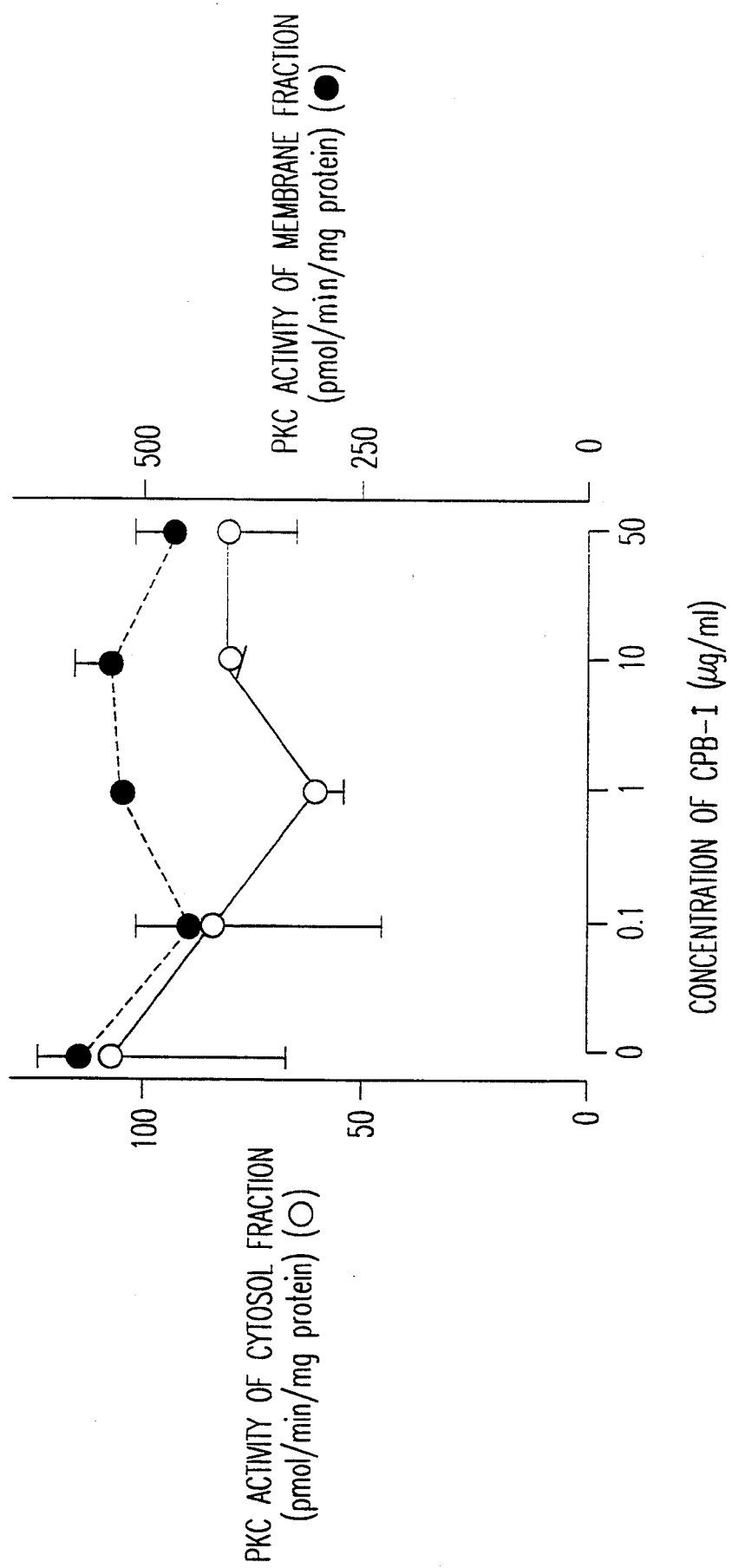
FIG. 3 is a diagram illustrating the experimental results as to an effect on the PKC activity in Experimental Example 4.

Experimental Example 4 Effect on PKC Activity 70-80% Confluent of HNEK was replaced to a KGM medium containing CPB-I, and incubated for 30 minutes. After incubation, cells were harvested, homogenized, fractionated to cytosol fraction and membrane fraction, and then measured their PKC activity using a PKC assay system (manufactured by Amersham Company). Each value in FIG. 3 indicates the mean value of three experiments. FIG. 3 indicates that CPB-I decreases the PKC activity.

Experimental Example 5 Effect on PKC Activation 70-80% Confluent of HNEK was replaced to a KGM medium separately containing CPB-I (10 μg/ml). After 30 minutes incubation, 10 ng/ml TPA was added thereto, and further incubated for the indicated periods of time. The cells were harvested, homogenized, fractionated to cytosol fraction and membrane fraction, and then measured the PKC activity using a PKC assay system (manufactured by Amersham Company) (FIG. 4).

Figure 4:
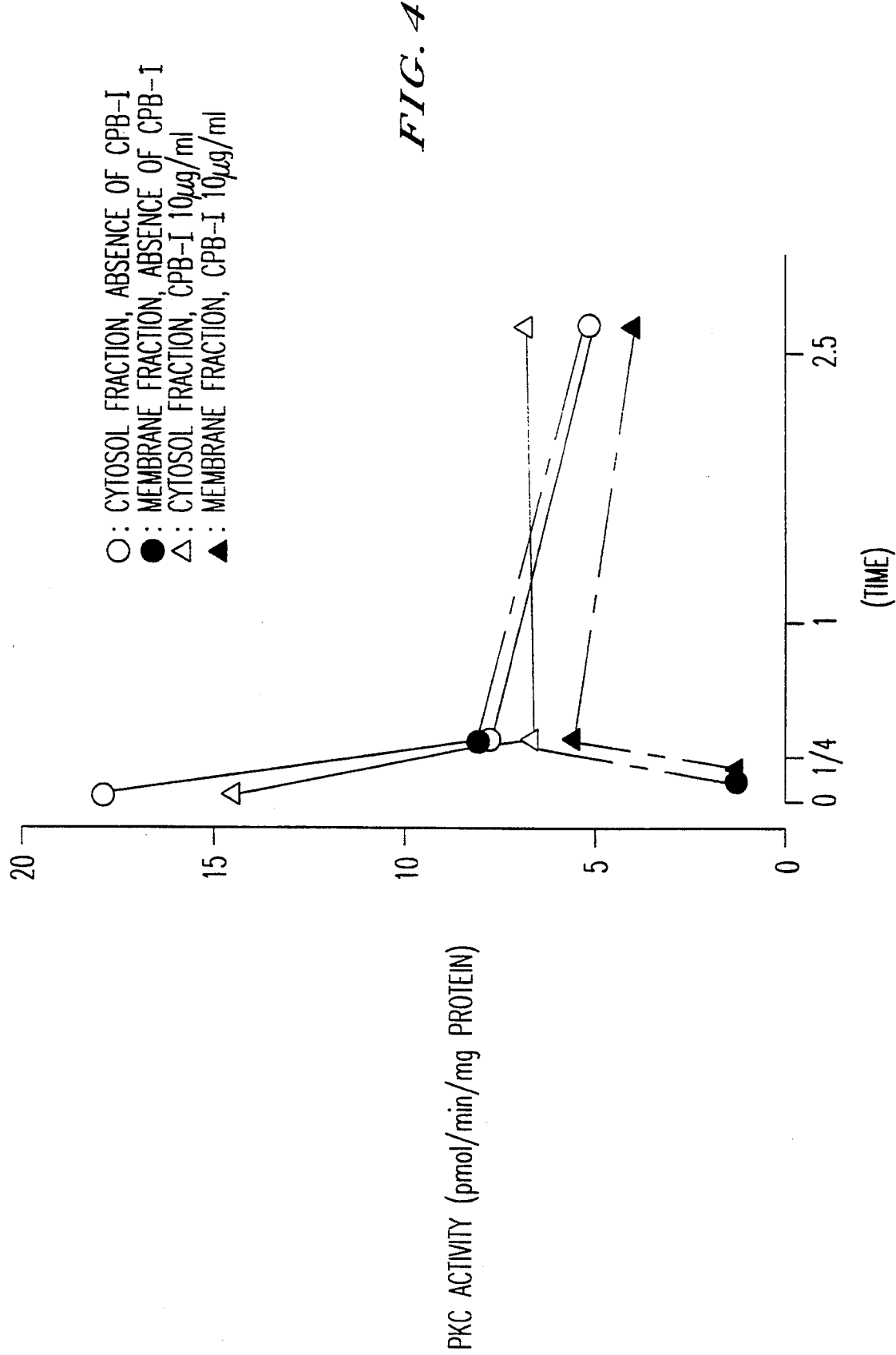
FIG. 4 is a diagram illustrating the experimental results as to an effect on the PKC activity in Experimental Example 5.

FIG. 4 indicates that CPB-I suppresses the activation of PKC by TPA.

Example 1

A creamy preparation having the following composition was produced according to a standard method.

| (Composition) | |
| --- | --- |
| CPB-I | 1-100 mg |
| White petrolatum | 4.0 g |
| Light liquid paraffin | 6.0 g |
| Cetyl alcohol | 3.0 g |
| Stearyl alcohol | 3.0 g |
| Isopropyl myristate | 4.0 g |
| Emulsifier | 3.5 g |
| Purified water | To 100.0 g |

A similar creamy preparation was also produced using recombinant CPB-I in place of CPB-1.

Example 2

A gel preparation having the following composition was produced according to a standard method.

| (Composition) | |
| --- | --- |
| CPB-I | 1-100 mg |
| Carboxyvinyl polymer | 0.5 g |
| Methyl cellulose | 0.2 g |
| Glycerol | 5.0 g |
| Sodium hydroxide | Proper amount |
| Purified water | To 100.0 g |

A similar gel preparation was also produced using recombinant CPB-I in place of CPB-1.

Example 3

An ophthalmic ointment having the following composition was produced according to a standard method.

| (Composition) | |
| --- | --- |
| CPB-I | 1-100 mg |
| Purified lanolin | 10.0 g |
| White petrolatum | To 100.0 g |

A similar ophthalmic ointment was also produced by using recombinant CPB-I in place of CPB-1.

Example 4

An ophthalmic solution having the following composition was produced according to a standard method.

| (Composition) | |
| --- | --- |
| CPB-I | 1-100 mg |
| 10% Benzalkonium chloride solution | 0.05 ml |
| Isotonic phosphate buffer solution | To 100.0 g |

A similar ophthalmic solution was also produced by using recombinant CPB-I in place of CPB-1.

Industrial Applicability

CPB-I and recombinant CPB-I, which are active ingredients in the therapeutic agents for skin or corneal diseases according to the present invention, have the excellent activities in promoting regeneration of granulation tissue, migration of corneal endothelial and epithelial cells, etc., and lowering PKC activity. Because these agents have an action mechanism different from that of the conventional agent, they can be used together with the conventional agent to enhance the therapeutic effect.

Therefore, the therapeutic agents for skin or corneal diseases according to the present invention are remarkably useful for treating all sorts of the skin and corneal diseases, in particular, wounds and psoriasis.

We claim:

1. A therapeutic composition suitable for topical application to the cornea, comprising CPB-I or recombinant CPB-I as the active ingredient, in a pharmaceutically acceptable carrier suitable for ophthalmic application.

2. The therapeutic composition as claimed in claim 1, which is suitable for treating a wound.

3. The therapeutic composition of claim 1 in the form of a cream, gel, solution, or ointment.

4. A therapeutic composition suitable for topical application to the skin, comprising CPB-I or recombinant CPB-I as the active ingredient, in a pharmaceutically acceptable carrier suitable for epidermal application.

5. The therapeutic composition of claim 4 which is suitable for treating a wound or psoriasis.

6. The therapeutic composition of claim 4 in the form of a cream, gel, solution, or ointment.

7. The therapeutic composition of claim 4 in the form of a cream, gel, or ointment.

8. A method of treating skin or corneal disease comprising topically administering a therapeutically effective amount of CPB-I or recombinant CPB-I in a pharmaceutical carrier suitable for topical application, to a subject in need thereof.

9. The method of claim 8 wherein said carrier comprises a gel, cream, solution, or ointment.

10. The method of claim 9 wherein said gel, cream, solution, or ointment is suitable for ophthalmic application.

11. The method of claim 8 wherein said skin disease is psoriasis.

12. The method of claim 8 wherein said skin disease is a wound.

13. The method of claim 8 wherein said corneal disease is a wound.

* * * * *